United States Patent
Suzuki et al.

(10) Patent No.: US 8,939,987 B2
(45) Date of Patent: Jan. 27, 2015

(54) ENDOSCOPE TREATMENT TOOL

(71) Applicant: Olympus Medical Systems Corp., Tokyo (JP)

(72) Inventors: Keita Suzuki, Tokyo (JP); Shunsuke Motosugi, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/855,125

(22) Filed: Apr. 2, 2013

(65) Prior Publication Data

US 2013/0289616 A1    Oct. 31, 2013

Related U.S. Application Data

(63) Continuation of application No. PCT/JP2012/079419, filed on Nov. 13, 2012.

(30) Foreign Application Priority Data

Mar. 13, 2012 (JP) ................. 2012-055887

(51) Int. Cl.
*A61B 17/26* (2006.01)
*A61B 17/00* (2006.01)
*A61B 17/29* (2006.01)
*A61B 19/00* (2006.01)

(52) U.S. Cl.
CPC ....... *A61B 17/00234* (2013.01); *A61B 17/2909* (2013.01); *A61B 17/29* (2013.01); *A61B 19/30* (2013.01); *A61B 2017/2911* (2013.01)
USPC ........................................ 606/113

(58) Field of Classification Search
USPC .......... 600/104; 606/106, 110, 113, 114, 127, 606/200
See application file for complete search history.

(56) References Cited

FOREIGN PATENT DOCUMENTS

| JP | A-10-290803 | 11/1998 |
|---|---|---|
| JP | A-2007-275386 | 10/2007 |
| JP | A-2010-201034 | 9/2010 |

OTHER PUBLICATIONS

International Search Report issued in International Patent Application No. PCT/JP2012/079419 dated Dec. 11, 2012 (with translation).

*Primary Examiner* — Ashley Fishback
(74) *Attorney, Agent, or Firm* — Oliff PLC

(57) ABSTRACT

An endoscope treatment tool includes a treatment portion, a manipulation portion, and a manipulation wire connecting the treatment portion and the manipulation portion, the manipulation portion includes a manipulation portion main body, a shaft, a clutch plate having a through-hole into which the shaft is slidably inserted, a manipulation member slidably attached to the manipulation portion main body, and a force adjustment member compressed in accordance with manipulation of the manipulation member, and the clutch plate is inclined with respect to the shaft in accordance with compression of the force adjustment member, and thereby the manipulation member is fixed to the manipulation portion main body by the clutch plate which is fixed to the shaft so as not to slide with respect to the shaft.

8 Claims, 11 Drawing Sheets

FIG. 13A
FIG. 13B
FIG. 13C
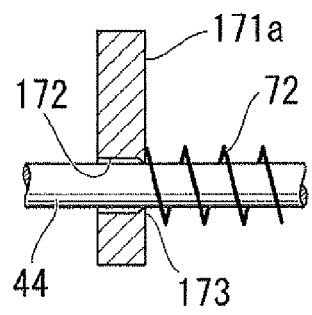
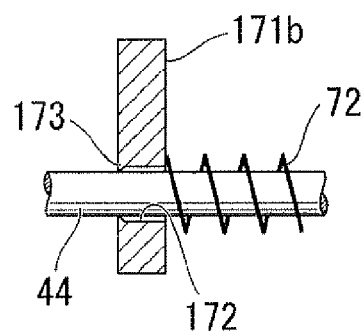
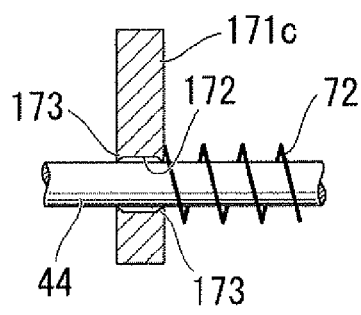
FIG. 14A
FIG. 14B
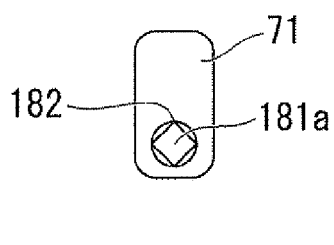
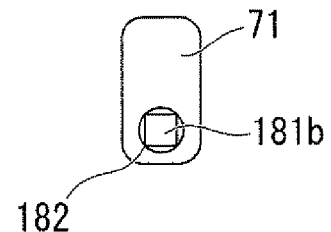
FIG. 15A
FIG. 15B
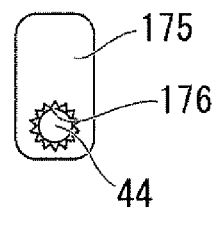
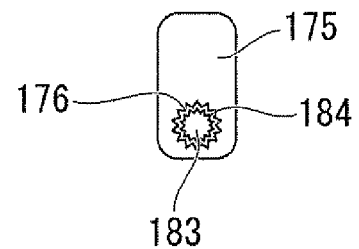

ENDOSCOPE TREATMENT TOOL

This application is a continuation application based on a PCT Patent Application No. PCT/JP2012/079419, filed Nov. 13, 2012, whose priority is claimed on Japanese Patent Application No. 2012-055887, filed Mar. 13, 2012. The contents of both the PCT Application and Japanese Application are incorporated herein by reference.

BACKGROUND OF THE INVENTION

1. Field of the Invention

The present invention relates to an endoscope treatment tool endoscopically inserted into a body cavity and used therein.

2. Description of Related Art

In the related art, a forceps having a pair of forceps members mutually and relatively rotatably supported via a rotation shaft is known as an endoscope treatment tool (hereinafter, simply referred to as a "treatment tool") having a flexible sheath and endoscopically inserted into a body cavity and used.

The pair of forceps members is connected to a manipulation portion in the proximal side via a manipulation wire. As the manipulation wire is advanced and retracted in an axial direction via the manipulation portion, the pair of forceps members can be relatively rotated about a rotation shaft to be opened and closed.

In such a forceps, when the manipulation wire is continued to be retracted even after the pair of forceps members is closed, a greater force is applied to the forceps members. For this reason, when the manipulation wire is excessively retracted in a state in which the forceps members grip a tissue or the like, a force of gripping the tissue is excessively increased. As a result, a load may be applied to the tissue.

In order to solve this problem, Japanese Unexamined Patent Application, First Publication No. H10-290803 discloses a treatment tool including a display unit configured to display a force applied to a treatment portion of a forceps member or the like in accordance with manipulation of a manipulation slider configured to advance or retract a manipulation wire. In the treatment tool, the force applied to the treatment portion is detected by deflection of an elastic body. An operator detects the force applied to the treatment portion by the display unit, and adjusts an amount of the manipulation of the manipulation slider. Accordingly, the operator can adjust the force.

SUMMARY OF THE INVENTION

According to a first aspect of the present invention, an endoscope treatment tool includes: a treatment portion which is provided at a distal end of the endoscope treatment tool; a manipulation portion which is configured to manipulate the treatment portion; and a manipulation wire which connects the treatment portion and the manipulation portion. The manipulation portion includes: a manipulation portion main body; a shaft which is attached to the manipulation portion main body and extends parallel to the manipulation portion main body; a clutch plate which has a through-hole into which the shaft is slidably inserted; a manipulation member which is slidably attached to the manipulation portion main body so as to manipulate the manipulation wire; and a force adjustment member which is compressed in accordance with manipulation of the manipulation member. The clutch plate is inclined with respect to the shaft such that a first axis of the through-hole is non-parallel to a second axis of the shaft in accordance with compression of the force adjustment member, and thereby the manipulation member is fixed to the manipulation portion main body by the clutch plate which is fixed to the shaft so as not to slide with respect to the shaft.

According to a second aspect of the present invention, in the endoscope treatment tool according to the first aspect, the manipulation portion may further include a posture holding member which is configured to hold a posture of the clutch plate such that the first axis of the through-hole is parallel to the second axis of the shaft. A posture holding by the posture holding member may be released by in accordance with the compression of the force adjustment member, and thereby the clutch plate may be inclined with respect to the shaft.

According to a third aspect of the present invention, in the endoscope treatment tool according to the second aspect, the manipulation member may include: a first slider which is connected to the manipulation wire and is slidably attached to the manipulation portion main body and the shaft; and a second slider which is slidably attached to the first slider. The second slider may be retracted with respect to the first slider, and thereby the force adjustment member may be compressed.

According to a fourth aspect of the present invention, in the endoscope treatment tool according to the third aspect, the treatment portion may be a pair of forceps members which is supported by a rotation shaft such that the forceps members freely rotate relative to each other.

According to a fifth aspect of the present invention, in the endoscope treatment tool according to the fourth aspect, an end portion of the clutch plate may come in contact with the second slider, and thereby the clutch plate may be inclined with respect to the shaft.

According to a sixth aspect of the present invention, in the endoscope treatment tool of the fourth aspect, the end portion of the clutch plate may project over an outer circumferential surface of the first slider.

According to a seventh aspect of the present invention, in the endoscope treatment tool according to the fourth aspect, the shaft and the manipulation wire may be concentrically disposed.

According to an eighth aspect of the present invention, in the endoscope treatment tool according to the fourth aspect, the posture holding member may be a bias spring biasing the clutch plate in a predetermined direction.

BRIEF DESCRIPTION OF THE DRAWINGS

FIG. 13A is a view showing a modified example of a clutch plate of the endoscope treatment tool according to each of the embodiments of the present invention.

FIG. 13B is a view showing a modified example of the clutch plate of the endoscope treatment tool according to each of the embodiments of the present invention.

FIG. 13C is a view showing a modified example of the clutch plate of the endoscope treatment tool according to each of the embodiments of the present invention.

FIG. 14A is a view showing a modified example of a shaft of the endoscope treatment tool according to each of the embodiments of the present invention.

FIG. 14B is a view showing a modified example of the shaft of the endoscope treatment tool according to each of the embodiments of the present invention.

FIG. 15A is a view showing a modified example of the clutch plate and the shaft of the endoscope treatment tool according to each of the embodiments of the present invention.

FIG. 15B is a view showing a modified example of the clutch plate and the shaft of the endoscope treatment tool according to each of the embodiments of the present invention.

DETAILED DESCRIPTION OF THE INVENTION

First Embodiment

An endoscope treatment tool according to a first embodiment of the present invention is described with reference to FIGS. 1 to 4.

Figure 1:
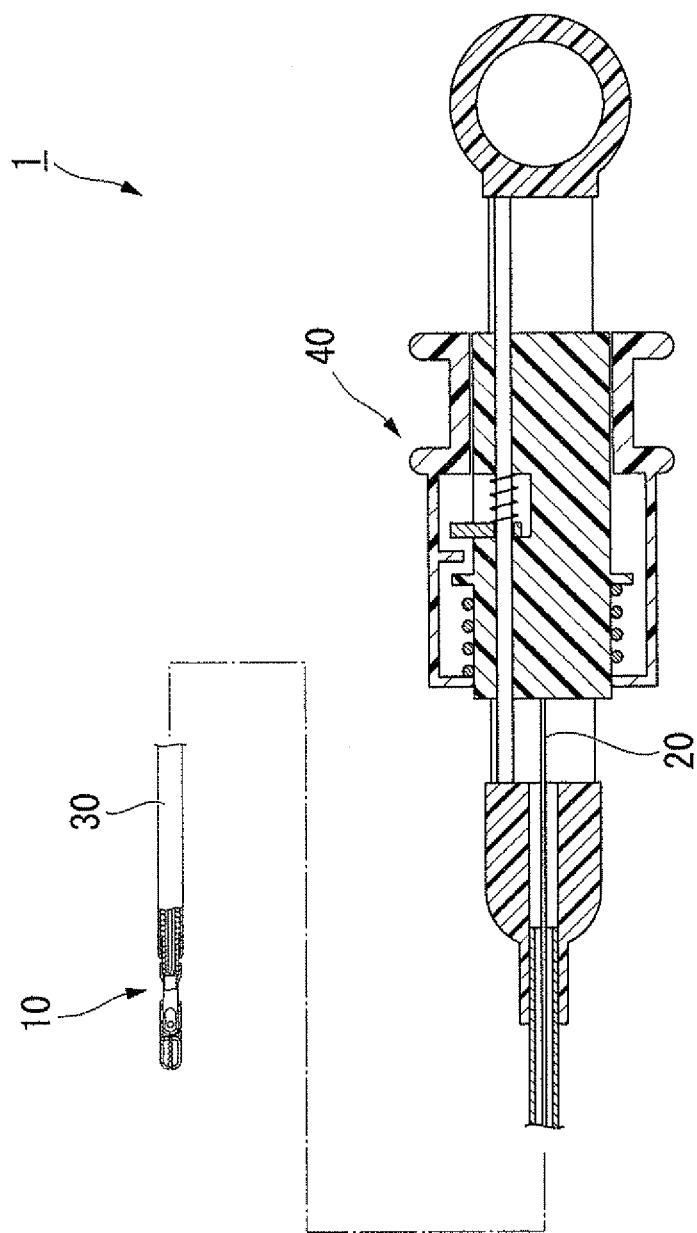
FIG. 1 is an overall view partially cross-sectionally showing an endoscope treatment tool according to a first embodiment of the present invention.

As shown in FIG. 1, a treatment tool 1, which is an endoscope treatment tool according to the present embodiment, includes a treatment portion 10, a manipulation portion 40, manipulation wires 20, and an insertion portion 30. The treatment portion 10 performs treatment with respect to a tissue in a body cavity. The manipulation portion 40 manipulates the treatment portion 10. The manipulation wires 20 connect the treatment portion 10 and the manipulation portion 40. The insertion portion 30 is formed to be long and is inserted into the body cavity.

Figure 2:
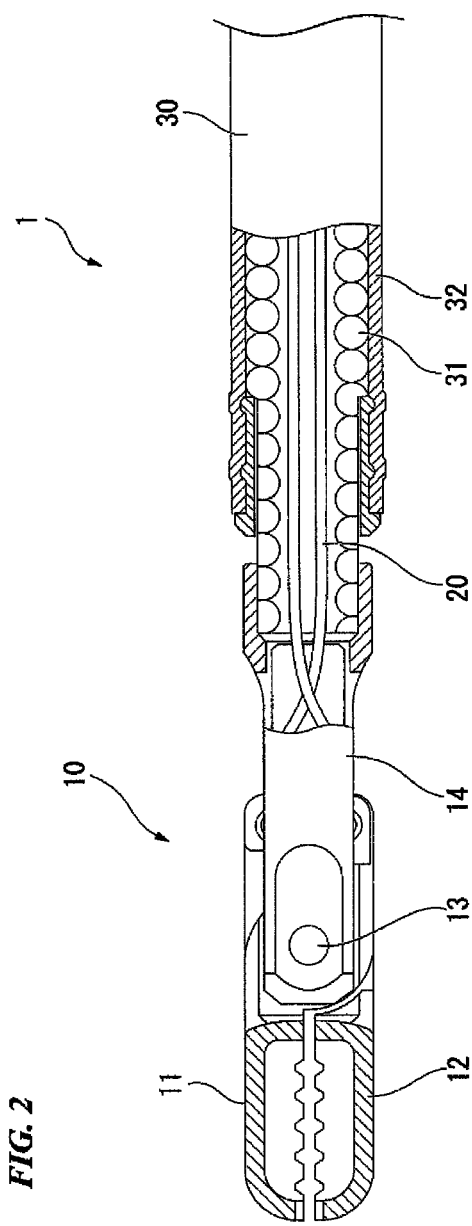
FIG. 2 is an enlarged view partially cross-sectionally showing a distal end portion of the endoscope treatment tool according to the first embodiment of the present invention.

FIG. 2 is an enlarged view partially cross-sectionally showing a distal end portion of the treatment tool 1 including the treatment portion 10. The treatment portion 10 is configured such that a pair of forceps members is connected and supported by a rotation shaft 13 so that the forceps members can freely rotate relative to each other. The pair of forceps members is constituted by a first forceps member 11 and a second forceps member 12. The rotation shaft 13 is supported by a cover member 14. The manipulation wires 20 are connected to a portion of each of the forceps members 11 and 12 closer to a proximal side thereof than the rotation shaft 13. The manipulation wires 20 are connected to the manipulation portion 40 through the inside of the insertion portion 30. In addition, in the present embodiment, the proximal sides of the manipulation wires 20 connected to the forceps members 11 and 12 are twisted and integrated with each other. For this reason, the manipulation wires 20 near the manipulation portion 40 are shown as an integrated state.

The insertion portion 30 has a long tubular shape into which the manipulation wires 20 are inserted. The insertion portion 30 has a coil sheath 31, and an insulated tube sheath 32 configured to cover the outside of the coil sheath 31. The cover member 14 is fixed to a distal end of the insertion portion 30. In the distal end of the insertion portion 30, the rotation shaft 13 is supported by the cover member 14 so as not to move relative to the cover member 14. A proximal end portion of insertion portion 30 is attached to the manipulation portion 40.

Figure 3A:
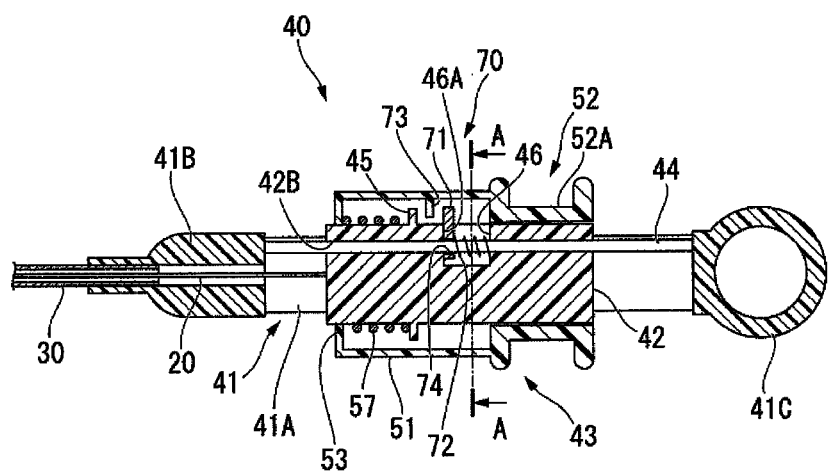
FIG. 3A is an enlarged cross-sectional view showing a manipulation portion of the endoscope treatment tool according to the first embodiment of the present invention.
Figure 3B:
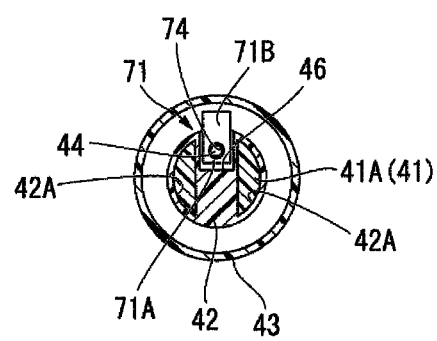
FIG. 3B is a cross-sectional view taken along a line A-A of FIG. 3A.

FIG. 3A is an enlarged cross-sectional view of the manipulation portion 40. FIG. 3B is a cross-sectional view taken along a line A-A of FIG. 3A. The manipulation portion 40 includes a manipulation portion main body 41, an inner slider (a manipulation member, a first slider) 42, and an outer slider (a manipulation member, a second slider) 43. The manipulation wires 20 are inserted into the manipulation portion main body 41. The inner slider 42 is slidably attached to the manipulation portion main body 41. The outer slider 43 is slidably attached to the inner slider 42.

The manipulation portion main body 41 is formed of a resin or the like. The manipulation portion main body 41 has a pair of intermediate portions 41A disposed substantially in parallel at an interval. The manipulation wires 20 are inserted between the pair of intermediate portions 41A. In addition, a shaft (to be described later) is disposed between the pair of intermediate portions 41A.

Tubular distal end portion 41B is attached to distal ends of the pair of intermediate portions 41A. A proximal end portion of the insertion portion 30 is connected to the distal end portion 41B. A handle 41C for a finger grip is mounted on the proximal end of the intermediate portions 41A. A shaft 44 is disposed between the pair of intermediate portions 41A so as to be substantially parallel to the intermediate portions 41A. The shaft 44 is fixed to the distal end portion 41B and the handle 41C at both ends of the shaft 44.

The inner slider 42 is formed of a resin or the like in a substantially columnar shape. A pair of through-holes 42A and a through-hole 42B are formed in the inner slider 42 to extend in an axial direction of the inner slider 42. The pair of intermediate portions 41A is inserted into the pair of through-holes 42A. The shaft 44 is inserted into the through-hole 42B. As the pair of intermediate portions 41A and the shaft 44 are inserted into the through-holes 42A and 42B, respectively, the inner slider 42 is attached to the manipulation portion main body 41 so as to be slidable with respect to the manipulation portion main body 41.

In an outer circumferential surface of the inner slider 42, a flange 45 projecting in a circumferential direction is formed at an intermediate part of the inner slider 42 in the axial direction. A notch 46 extending to the through-hole 42B is formed at the proximal side rather than at the flange 45. A portion of the shaft 44 is exposed in the notch 46.

The outer slider 43 is formed of a resin or the like in a substantially tubular shape. The manipulation portion main body 41 and the inner slider 42 are inserted into the inner cavity of the outer slider 43.

The outer slider 43 is constituted by a first tubular portion 51 formed at a distal side thereof, and a second tubular portion 52 connected to the proximal end of the first tubular portion 51. A finger grip portion 52A which a user grips with his/her finger is formed at the second tubular portion 52. A portion of the inner slider 42 at which the flange 45 is formed is inserted into the first tubular portion 51. For this reason, the diameter of the inner cavity of the first tubular portion 51 is larger than that of the inner cavity of the second tubular portion 52.

A distal wall portion 53 is formed at the distal end of the first tubular portion 51. Accordingly, an inside diameter of an opening of the distal end of the first tubular portion 51 is slightly larger than an outside diameter of the inner slider 42. A coil spring 57 (a force adjustment member) is disposed between the distal wall portion 53 and the flange 45. A portion of the inner slider 42 closer to the distal side thereof than the flange 45 is inserted into the coil spring 57. That is, as the outer slider 43 is slid toward the proximal side with respect to the inner slider 42, the coil spring 57 is compressed between the distal wall portion 53 and the flange 45. In a state in which the coil spring 57 is not compressed, the coil spring 57 keeps a distance between the distal wall portion 53 and the flange 45 constant. For this reason, when the outer slider 43 is slid toward the proximal side with respect to the manipulation portion main body 41, the outer slider 43 and the inner slider 42 are integrally moved.

A force holding mechanism 70 is provided at the inner slider 42 and the outer slider 43. The force holding mechanism 70 holds a force applied to a substance gripped by the treatment portion 10 at a predetermined value or less. The force holding mechanism 70 includes a clutch plate 71 and a projection 73. The clutch plate 71 is disposed in the notch 46 of the inner slider 42. The projection 73 is formed at the inner wall of the first tubular portion 51 of the outer slider 43.

The clutch plate 71 is a plate-shaped member formed of a metal, a resin, or the like. The clutch plate 71 has a through-hole 74 formed in a thickness direction and passing through one end portion 71A in a longitudinal direction. An inside diameter of the through-hole 74 is slightly larger than an outside diameter of the shaft 44. The clutch plate 71 is disposed in the notch 46 in a state in which the shaft 44 is inserted into the through-hole 74. Further, the clutch plate 71 is disposed such that the other end portion 71B in the longitudinal direction projects from an outer circumferential surface of the inner slider 42. A bias spring (a posture holding member) 72 is disposed at a portion in the notch 46 closer to the proximal side than the clutch plate 71. The bias spring 72 biases the clutch plate 71 toward the distal side of the notch 46 such that the clutch plate 71 comes in contact with a wall surface 46A of the distal side of the notch 46. In the present embodiment, a compression coil spring is used as the bias spring 72.

The projection 73 projects from the inner wall of the inner cavity of the first tubular portion 51 at a position closer to the proximal side than the flange 45 formed at the inner slider 42. A projection height of the projection 73 is a value such that the projection 73 comes in contact with the end portion 71B of the clutch plate 71 to change an angle formed by the clutch plate 71 and the shaft 44 when the outer slider 43 is slid toward the proximal side with respect to the inner slider 42. Further, the projection height of the projection 73 is a value such that a surface of the distal side of the projection 73 comes in contact with a surface of the proximal side of the flange 45 when the outer slider 43 is slid toward the distal side with respect to the inner slider 42.

The proximal end portion of the manipulation wire 20 is fixed to the inner slider 42. As the inner slider 42 is slid with respect to the manipulation portion main body 41, the manipulation wire 20 is advanced and retracted. The pair of forceps members 11 and 12 of the treatment portion 10 can be opened and closed by a movement of the manipulation wire 20.

An operation in use of the treatment tool 1 configured as described above is described.

First, an endoscope (not shown) is inserted into a patient's body. A distal end of the endoscope is moved to the vicinity of a tissue (a target tissue) in a body cavity of a treatment target.

A user grips the finger grip portion 52A with his/her finger and slides the outer slider 43 toward the proximal side of the manipulation portion main body 41 (hereinafter, the movement in this direction is referred to as "retract"). Accordingly, the inner slider 42 is retracted with the outer slider 43, and the pair of forceps members 11 and 12 is closed. In this state, the treatment portion 10 and the insertion portion 30 are inserted into a forceps channel of the endoscope. The treatment portion 10 projects from a distal end of the forceps channel.

The user manipulates the manipulation portion 40 and performs treatment of the target tissue by the treatment portion 10 while observing the target tissue with the endoscope.

The outer slider 43 is slid toward the distal side of the manipulation portion main body 41 (hereinafter, the movement in this direction is referred to as "advance") to open the pair of forceps members 11 and 12. The outer slider 43 advances with respect to the inner slider 42, and the projection 73 comes in contact with the flange 45. After that, the inner slider 42 advances with the outer slider 43. The manipulation wire 20 connected to the inner slider 42 advances. As described above, the rotation shaft 13 is supported by the cover member 14 attached to the insertion portion 30. For this reason, the first forceps member 11 and the second forceps member 12 are rotated about the rotation shaft 13 fixed to the insertion portion 30, respectively. Accordingly, the treatment portion 10 is opened.

In addition, in a state in which the coil spring 57 is not compressed, as shown in FIG. 3A, the clutch plate 71 is pressed against the wall surface 46A of the notch 46 by the bias spring 72. That is, a posture of the clutch plate 71 is held such that an axis of the through-hole 74 is parallel (including substantially parallel) to an axis of the shaft 44. For this reason, an inner surface of the through-hole 74 hardly comes in contact with an outer surface of the shaft 44. Accordingly, the inner slider 42 and the outer slider 43 substantially smoothly advance and retract with respect to the manipulation portion main body 41.

The target tissue is disposed between the first forceps member 11 and the second forceps member 12. In this state, when the user retracts the outer slider 43, the target tissue is sandwiched and gripped between the first forceps member 11 and the second forceps member 12.

Even after the target tissue is sandwiched, the outer slider 43 can be slightly retracted. However, when the target tissue is somewhat compressed, the outer slider 43 cannot be retracted any more. In this state, when the outer slider 43 is further pulled to be retracted, the pulling force is transmitted to the pair of forceps members 11 and 12 via the manipulation wire 20. For this reason, a gripping force applied to the target tissue is increased.

Figure 4:
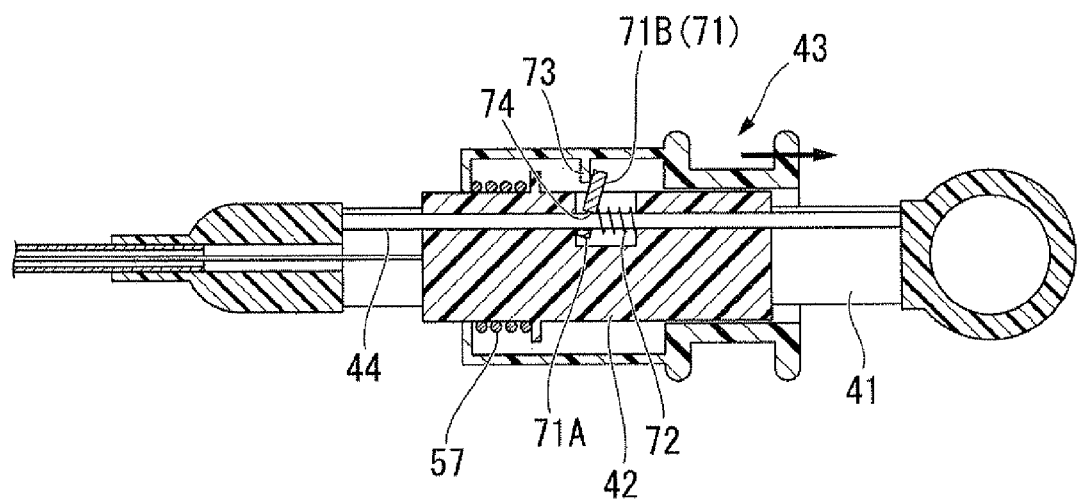
FIG. 4 is a view showing a movement of the manipulation portion upon use of the endoscope treatment tool according to the first embodiment of the present invention.

When the magnitude of the force for pulling the outer slider 43 is increased to a magnitude in which the coil spring 57 can be compressed, as shown in FIG. 4, the outer slider 43 compresses the coil spring 57 and retracts with respect to the inner slider 42.

When the outer slider 43 is retracted with respect to the inner slider 42 by a predetermined amount, the projection 73 comes in contact with the end portion 7113 of the clutch plate 71. When the outer slider 43 is further retracted, the end portion 71B is moved toward the proximal side by the projection 73. However, since the end portion 71A is biased toward the distal side by the bias spring 72, the end portion 71A is not moved toward the proximal side with the end portion 71B. As a result, as shown in FIG. 4, the clutch plate 71 is inclined such that the axis of the through-hole 74 is not parallel to the axis of the shaft 44. Further, an edge of the end portion 71A side in an opening of the distal side of the through-hole 74 and an edge of the end portion 71B side in an opening of the proximal side of the through-hole 74 come in contact with the shaft 44. For this reason, a frictional force generated between the clutch plate 71 and the shaft 44 is increased.

The clutch plate 71 is fixed to the shaft 44 by the increased frictional force. As a result, the inner slider 42 is held such that the inner slider 42 is substantially unslidable with respect to the manipulation portion main body 41. As a result, even when the outer slider 43 is retracted, the pulling force applied to the manipulation wire 20 is not increased. For this reason, the gripping force applied from the treatment portion 10 to the target tissue is kept constant.

According to the treatment tool 1 according to the present embodiment, when the force for pulling the outer slider 43 reaches a predetermined magnitude, first, the coil spring 57 is compressed. Next, interlocking of the inner slider 42 and the outer slider 43 is released. Accordingly, applying an excessive force to the target tissue gripped by the treatment portion 10 is suppressed.

Further, when the coil spring 57 is compressed to a predetermined amount, the projection 73 of the force holding mechanism 70 comes in contact with the clutch plate 71 to incline the clutch plate 71 with respect to the shaft 44. For this reason, a frictional force generated between the clutch plate 71 and the shaft 44 is increased. The inner slider 42 connected to the manipulation wire 20 is fixed to the manipulation portion main body 41 by such a movement of the force holding mechanism 70. For this reason, the force applied to the gripped target tissue is maintained so as not to be increased any more.

Accordingly, applying an excessive gripping force to the gripped target tissue can be prevented by simply performing the same manipulation as the treatment tool of the related art in which the slider is pulled to be retracted with respect to the manipulation portion main body. Further, the gripping force can be easily maintained at a predetermined value or less. As a result, the target tissue can be more safely treated through easy manipulation.

The inner slider 42 is fixed to the manipulation portion main body 41 based on the force applied to the slider, other than a positional relation between the slider and the manipulation portion main body, or a movement amount of the slider with respect to the manipulation portion main body. For this reason, even when an initial position of the slider with respect to the manipulation portion main body is changed due to serpentine movement or the like of the insertion portion 30 in the forceps channel of the endoscope, a magnitude of the maximum force applied to the treatment portion 10 is not changed. Accordingly, the maximum value of the gripping force generated at the treatment portion can be controlled to be a predetermined value or less with no influence due to variation in the usage environment of the treatment tool 1, which is changed each time.

A timing at which interlocking of the inner slider 42 and the outer slider 43 is released can be appropriately adjusted by replacing the coil spring 57 with a new one having a different spring constant, or the like. In addition, a timing at which the inner slider 42 is fixed to the manipulation portion main body 41 can be appropriately adjusted by changing a distance between the projection 73 and the end portion 71B of the clutch plate 71 in a state before the coil spring 57 is compressed.

Second Embodiment

An endoscope treatment tool according to a second embodiment of the present invention is described with reference to FIG. 5. A treatment tool 81 according to the present embodiment is different from the treatment tool 1 according to the first embodiment in that the bias spring is not provided.

In addition, in the following description, common elements with the treatment tool according to the embodiment as described above are designated by the same reference numerals, and a description thereof is not repeated here.

Figure 5:
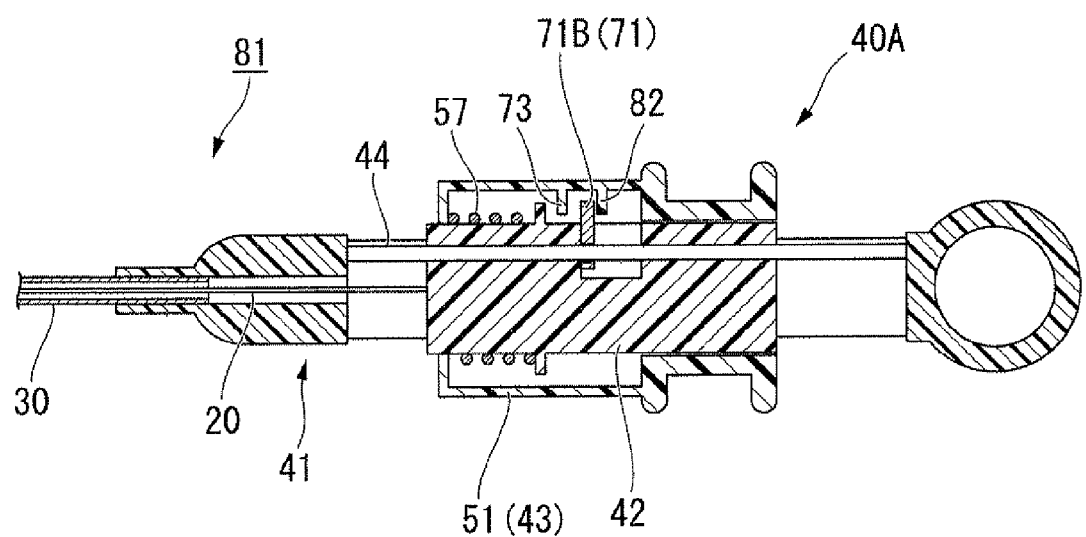
FIG. 5 is an enlarged cross-sectional view showing a manipulation portion of an endoscope treatment tool according to a second embodiment of the present invention.

FIG. 5 is a partially enlarged cross-sectional view showing the manipulation portion 40A of the treatment tool 81. A structure of the manipulation portion 40A is substantially the same as that of the manipulation portion 40 of the treatment tool 1. However, in the manipulation portion 40A, no bias spring is attached to the shaft 44. In addition, a second projection 82 having a projection length such that the second projection 82 can come in contact with the clutch plate 71 is formed at an inner surface of the first tubular portion 51 of the outer slider 43. In a state in which the coil spring 57 is not compressed, the second projection 82 is disposed closer to the proximal side than the end portion 71B of the clutch plate 71. The projection 73 and the second projection 82 are disposed such that the end portion 71B is sandwiched therebetween in the axial direction of the shaft 44.

A method for using the treatment tool 81 is almost the same as that of the treatment tool 1. When the outer slider 43 is retracted with respect to the inner slider 42 while compressing the coil spring 57, the clutch plate 71 is inclined with respect to the shaft 44. For this reason, the gripping force generated at the treatment portion 10 (not shown) is maintained so as not to be increased any more.

When the user reduces the pulling force applied to the outer slider 43, the outer slider 43 advances with respect to the inner slider 42. Here, in the treatment tool 1, the clutch plate is returned to its original posture by the bias spring. On the other hand, in the treatment tool 81 according to the embodiment, as the second projection 82 comes in contact with the end portion 71B to press the end portion 71B toward the distal side, the clutch plate 71 returns to its original posture. For this reason, the posture is maintained.

Like the above-described treatment tool 1, applying an excessive gripping force to the gripped target tissue can also be prevented by the treatment tool 81 according to the present embodiment. Further, the gripping force can be easily held at a predetermined value or less.

The treatment tool 81 does not require a bias spring. For this reason, the number of parts can be reduced and manufacturing cost can be reduced by integrally forming the projection 73 and the second projection 82 with the outer slider, or the like.

Third Embodiment

An endoscope treatment tool according to a third embodiment of the present invention is described with reference to FIGS. 6A to 7. A treatment tool 91 according to the present embodiment is different from the treatment tool according to the above-described embodiments in that a shaft and a manipulation wire are concentrically disposed.

Figure 6A:
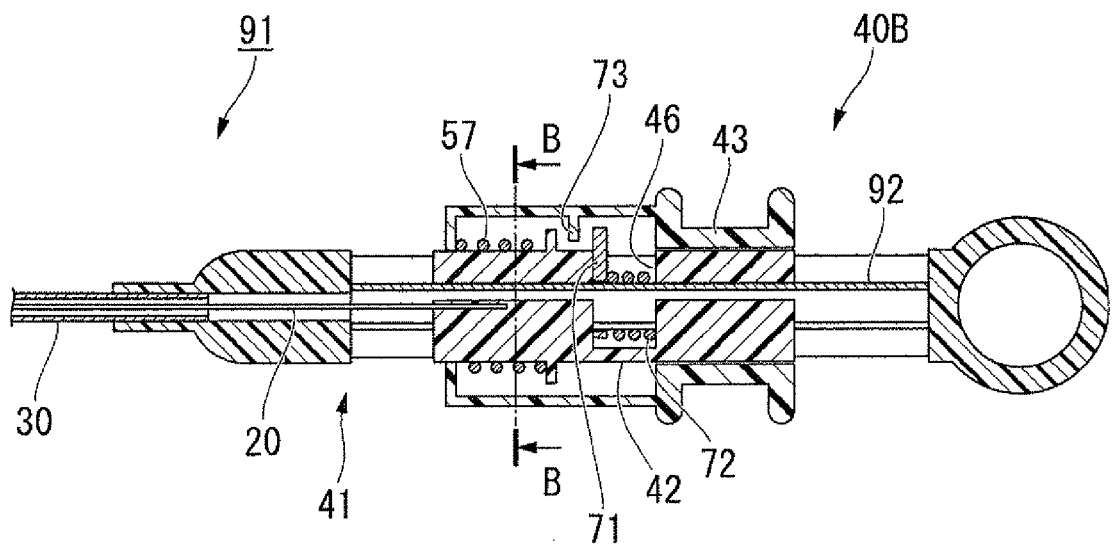
FIG. 6A is an enlarged cross-sectional view showing a manipulation portion of an endoscope treatment tool according to a third embodiment of the present invention.
Figure 6B:
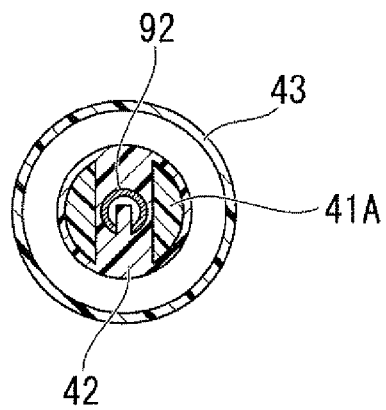
FIG. 6B is a cross-sectional view taken along a line B-B of FIG. 6A.

FIG. 6A is a partially enlarged cross-sectional view showing the manipulation portion 40B of the treatment tool 91. FIG. 6B is a cross-sectional view taken along a line B-B of FIG. 6A. As shown in FIGS. 6A and 6B, a shaft 92 has a C-shaped cross-section in the radial direction. The cross-sectional shape can be formed by removing a portion of an outer circumferential surface of a pipe-shaped member in the axial direction.

The shaft 92 is inserted into the inner slider 42 to be concentrically (including substantially concentrically; the same applies hereinafter) disposed in the inner slider 42 having a substantially columnar shape. The proximal end portion of the manipulation wire 20 is inserted into the shaft 92 to be connected to the inner slider 42. The manipulation wire 20, the shaft 92 and the inner slider 42 are concentrically disposed.

The shaft 92 is different from the above-described shaft 44 in a shape and a position at which the shaft 92 is inserted into the inner slider. For this reason, the notch 46, the clutch plate 71, and the bias spring 72 may have dimensions or the like different from those of the first embodiment. However, since the basic structure and function are the same as those of the first embodiment, the same reference numerals are designated. In addition, an operation in use of the treatment tool 91 is also substantially the same as that of the treatment tool 1.

Like the above-described treatment tool 1, applying an excessive gripping force to the gripped target tissue can be prevented by the treatment tool 91 according to the present embodiment. Further, the gripping force can be easily held at a predetermined value or less.

Since the shaft and the manipulation wire are concentrically disposed, a dimension in the radial direction of the inner slider can be further reduced. As a result, a dimension in the radial direction of the outer slider can also be reduced. Accordingly, a reduction in size of the manipulation portion becomes possible.

Figure 7:
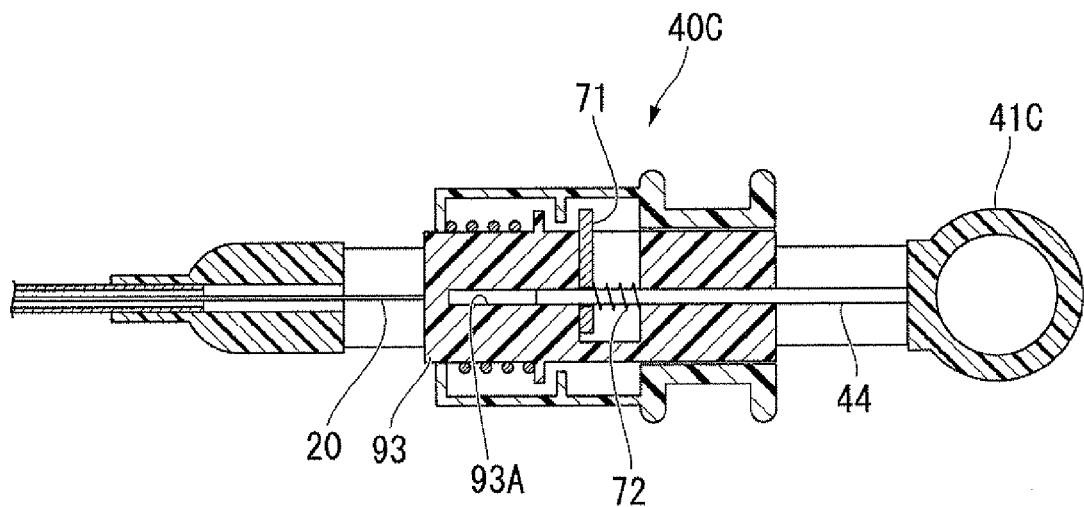
FIG. 7 is an enlarged cross-sectional view showing a manipulation portion of a modified example of the endoscope treatment tool according to the third embodiment of the present invention.

FIG. 7 is a partially enlarged cross-sectional view showing a manipulation portion 40C according to a modified example of the endoscope treatment tool according to the present embodiment. The shaft 44 has the same rod shape as the first embodiment. Only the proximal end of the shaft 44 is fixed to the handle 41C. The distal end of the shaft 44 is inserted into a bottomed hole 93A formed in an inner slider 93. The hole 93A is opened at the wall surface 46A in the inner slider 93 toward the distal side. The depth of the hole 93A is a value such that a bottom surface of the hole 93A does not come in contact with the distal end of the shaft 44 even when the inner slider 93 is fully retracted. A connection state between the manipulation wire 20 and the inner slider 93 is the same as that of the endoscope treatment tool according to the first embodiment.

As described above, even when a rod-shaped shaft is used, the shaft and the manipulation wire can be concentrically disposed.

Fourth Embodiment

An endoscope treatment tool according to a fourth embodiment of the present invention is described with reference to FIG. 8. A treatment tool 101 according to the present embodiment is different from the treatment tool according to each of the above-described embodiments in that the projection configured to incline the clutch plate is not provided.

Figure 8:
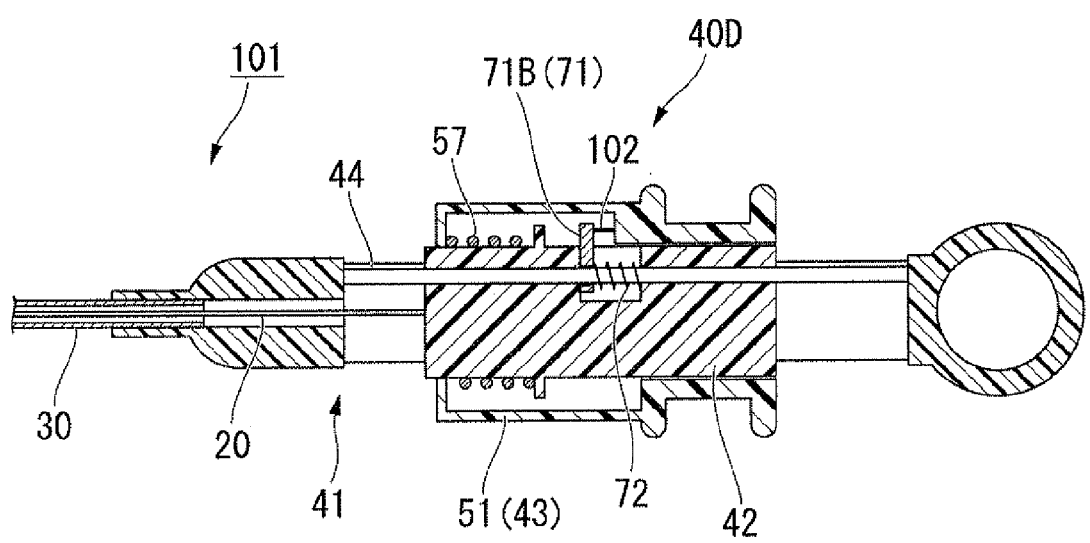
FIG. 8 is an enlarged cross-sectional view showing a manipulation portion of an endoscope treatment tool according to a fourth embodiment of the present invention.

FIG. 8 is a partially enlarged cross-sectional view showing a manipulation portion 40D of a treatment tool 101. No projection is formed at the inner wall of the outer slider 43. Instead, the end portion 71B of the clutch plate 71 and the proximal end of the first tubular portion 51 are connected by a connecting member 102. The distance between the end portion 71B and the proximal end of the first tubular portion 51 can be kept substantially constant by the connecting member 102.

In the treatment tool 101, when the outer slider 43 is retracted with respect to the inner slider 42, the connecting member 102 pulls the end portion 71B of the clutch plate 71 toward the proximal side. As a result, the clutch plate 71 is inclined. Accordingly, like the treatment tool according to each of the above-described embodiments, applying an excessive gripping force to the gripped target tissue can be prevented. Further, the gripping force can be easily held at a predetermined value or less.

There is no need to maintain a space in which the projection 73 is formed at the first tubular portion 51 of the outer slider 43. For this reason, a dimension in the axial direction of the inner slider 42 and the outer slider 43 can be reduced. The manipulation portion can be further reduced.

In the present embodiment, the connecting member preferably has a high stiffness from a viewpoint in which the clutch plate is securely inclined with respect to the shaft. As the clutch plate is inclined, a connecting portion between the connecting member and the clutch plate is displaced as it approaches the shaft. For this reason, it is preferable that the connecting member has slight flexibility so that the displacement can be absorbed.

Fifth Embodiment

An endoscope treatment tool according to a fifth embodiment of the present invention is described with reference to FIGS. 9 to 10B. The disposition of a clutch plate of a treatment tool 111 according to the present embodiment is different from the disposition of the clutch plate of the treatment tool according to each of the above-described embodiments.

Figure 9:
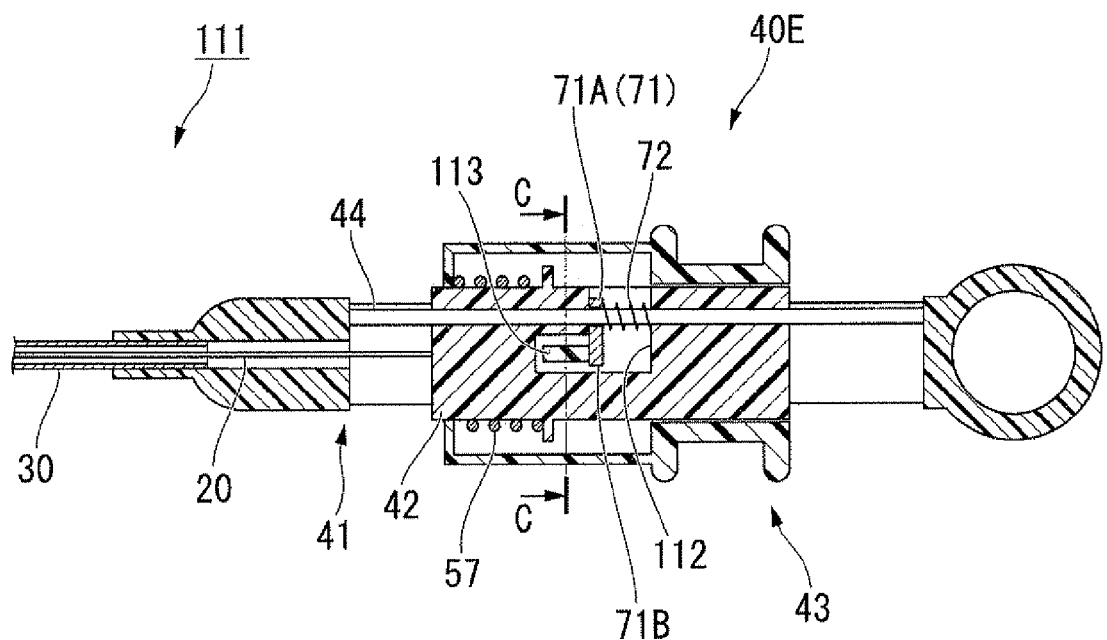
FIG. 9 is an enlarged cross-sectional view showing a manipulation portion of an endoscope treatment tool according to a fifth embodiment of the present invention.
Figure 10A:
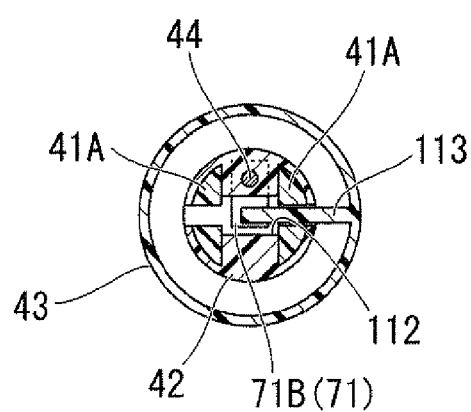
FIG. 10A is a cross-sectional view taken along a line C-C of FIG. 9.
Figure 10B:
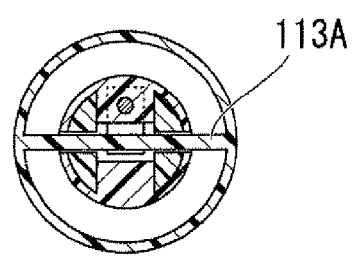
FIG. 10B is a cross-sectional view of a portion corresponding to FIG. 10A of a modified example of the endoscope treatment tool according to the fifth embodiment of the present invention.

FIG. 9 is a partially enlarged cross-sectional view showing a manipulation portion 40E of the treatment tool 111. FIG. 10A is a cross-sectional view taken along a line C-C of FIG. 9. A notch 112 formed in the inner slider 42 is formed to have a larger depth than that of the notch 46 of the first embodiment or the like. Further, the bottom portion of the notch 112 extends toward the distal side. As shown in FIG. 10A, the notch 112 extends in a direction perpendicular to the axis of the inner slider 42 to pass through the inner slider 42.

In the clutch plate 71, the end portion 71B in which the through-hole 74 is not formed is disposed toward the bottom portion of the notch 112. The clutch plate 71 is disposed so as not to project over the outer circumferential surface of the inner slider 42.

Instead of the projection 73, a projection 113 is formed at the outer slider 43. As shown in FIG. 10A, the projection 113 enters the notch 112 from the opening of the bottom portion of the notch 112. The projection 113 is disposed in a state in which the projection 113 can come in contact with the end portion 71B of the clutch plate 71. A groove extending in a longitudinal direction of the intermediate portion 41A is formed at the intermediate portion 41A of the manipulation portion main body 41, which is inserted into the inner slider 42, to correspond to a position of the projection 113. For this reason, the projection 113 does not interfere with advance and retraction of the inner slider 42 and the outer slider 43 with respect to the manipulation portion main body 41.

An operation in use of the treatment tool 111 is almost the same as that of the first embodiment. When the outer slider 43 is retracted with respect to the inner slider 42, the end portion 71B of the clutch plate 71 is retracted by the projection 113. As a result, the clutch plate 71 is inclined with respect to the shaft 44.

In the treatment tool 111 according to the present embodiment, like the treatment tool according to each of the above-described embodiments, applying an excessive gripping force to the gripped target tissue can be prevented. Further, the gripping force can be easily held at a predetermined value or less.

Since the clutch plate 71 can be disposed not to project over the outer circumferential surface of the inner slider 42, the size of the manipulation portion can be easily reduced.

In the present embodiment, an example of "a cantilever" in which the projection 113 is supported by one part of the inner wall of the outer slider has been described. Alternatively, like a modified example shown in FIG. 10B, a projection 113A of "a double-supported beam" in which the projection is supported by two parts of the inner wall may be provided. In this case, since strength of the projection is increased, a movement of inclining the clutch plate can be further stabilized.

Sixth Embodiment

An endoscope treatment tool according to a sixth embodiment of the present invention is described with reference to FIGS. 11 and 12. A treatment tool 121 according to the present embodiment is different from the treatment tool according to each of the above-described embodiments in that the relationship between the inner slider and the outer slider is reversed.

Figure 11:
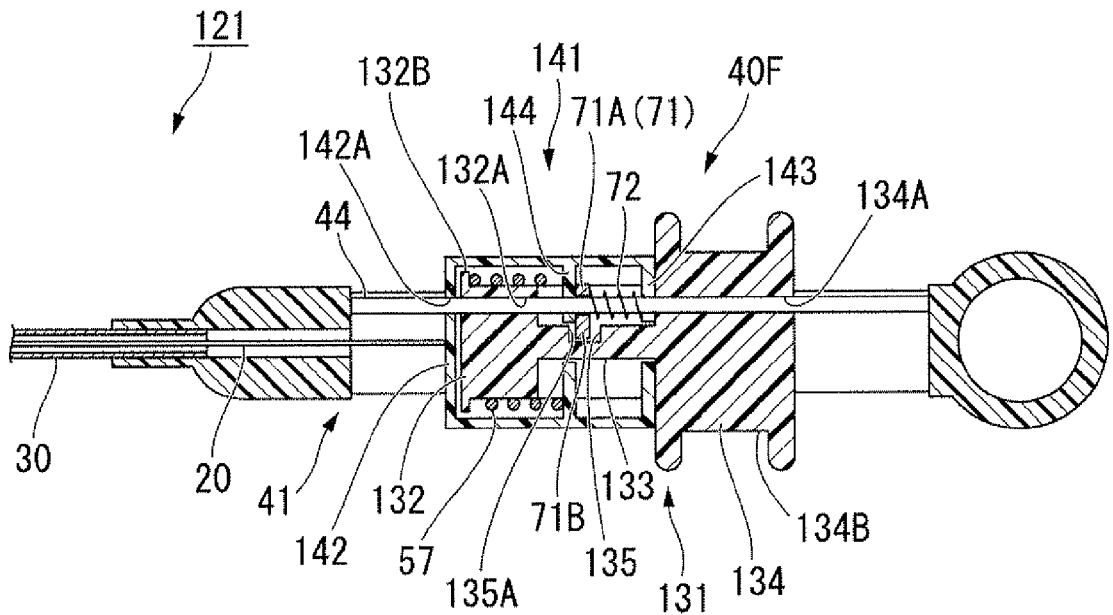
FIG. 11 is an enlarged cross-sectional view showing a manipulation portion of an endoscope treatment tool according to a sixth embodiment of the present invention.

FIG. 11 is a partially enlarged cross-sectional view showing a manipulation portion 40F of a treatment tool 121. An inner slider 131 has a distal end portion 132, an intermediate portion 133, and a proximal end portion 134 in sequence from a distal side thereof.

The distal end portion 132 has a through-hole 132A and a flange 13213. The shaft 44 is inserted into the through-hole 132A. The flange 13213 is formed at the distal end of the distal end portion 132 and projects in the radial direction. The distal end portion 132 has a substantially columnar shape.

The proximal end portion 134 is formed in a substantially columnar shape having a larger diameter than the distal end portion 132. The proximal end portion 134 has a through-hole 134A through which the shaft 44 is inserted, and a finger grip portion 134B.

The intermediate portion 133 has a notch 135 formed in an outer circumferential surface thereof. The intermediate portion 133 is formed in a substantially columnar shape having a smaller diameter than the distal end portion 132 and the proximal end portion 134. The intermediate portion 133 connects the distal end portion 132 and the proximal end portion 134.

An outer slider 141 has a substantially cylindrical shape. The outer slider 141 has a first end surface 142 of a distal end thereof, a second end surface 143 of a proximal end thereof, and a partition 144 formed at an intermediate portion thereof. A through-hole 142A into which the shaft 44 is inserted is formed in the first end surface 142. A proximal end portion of the manipulation wire 20 is connected to the first end surface 142. Shapes of the second end surface 143 and the partition 144 are not restricted as long as the shaft 44 is inserted into each of them and they do not interfere with the advance and retraction of the intermediate portion 133 of the inner slider 131.

As shown in FIG. 11, the distal end portion 132 of the inner slider 131 is disposed in a space between the first end surface 142 and the partition 144 in the outer slider 141. The coil spring 57 is disposed between the flange 132B and the partition 144 in the outer slider 141. The proximal end portion 134 is disposed closer to the proximal side than the second end surface 143. The length in the axial direction of the distal end portion 132 is smaller than a distance between the first end surface 142 and the partition 144. For this reason, the inner slider 131 can compress the coil spring 57 to retract to a certain length with respect to the outer slider 141.

The clutch plate 71 attached to the shaft 44 is disposed in a space between the partition 144 and the second end surface 143 in the outer slider 141. The bias spring 72 is disposed between the clutch plate 71 and the second end surface 143. The bias spring 72 biases the end portion 71A of the clutch plate 71 toward the partition 144. The end portion 71B of the clutch plate 71 enters the notch 135 formed in the intermediate portion 133 of the inner slider 131. A wall surface 135A of the distal side of the notch 135 is disposed to come in contact with the end portion 71B when the inner slider 131 is retracted with respect to the outer slider 141.

In use of the treatment tool 121, the user grips the finger grip portion 134B of the inner slider 131 with his/her finger to manipulate the advance and retraction of the inner slider 131 and the outer slider 141. When the inner slider 131 is continuously pulled even after the treatment portion 10 is closed, the coil spring 57 is compressed in a short time and the inner slider 131 is retracted with respect to the outer slider 141. Then, the wall surface 135A of the notch 135 formed in the intermediate portion 133 comes in contact with the end portion 71B of the clutch plate 71, and the end portion 71B is retracted with respect to the shaft 44. As a result, the clutch plate 71 is inclined with respect to the shaft 44.

That is, in the treatment tool 121 according to the present embodiment, the outer slider 141 functions as a first slider, and the inner slider 131 functions as a second slider. Accordingly, like the treatment tool according to each of the above-described embodiments, friction between the clutch plate and the shaft is increased and the maximum value of the gripping force generated at the treatment portion 10 is controlled to be a predetermined value or less.

As described above, in the treatment tool according to each of the embodiments of the present invention, a positional relation between the first slider and the second slider can be reversed. For this reason, various variations in specific structures can be made. In addition, the treatment tool can be configured while flexibly coping with various restrictions in manufacture.

Figure 12:
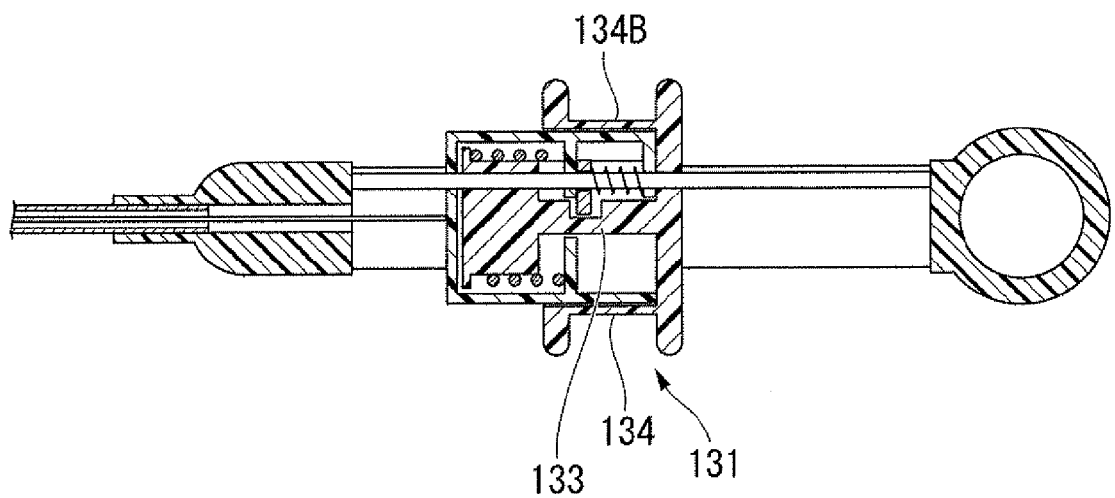
FIG. 12 is an enlarged cross-sectional view showing a manipulation portion of a modified example of the endoscope treatment tool according to the sixth embodiment of the present invention.

In the treatment tool according to the present embodiment, like a modified example shown in FIG. 12, the proximal end portion 134 of the inner slider 131 may have a cylindrical shape. At least a portion of the finger grip portion 134B may be disposed to overlap the intermediate portion 133 in the axial direction of the inner slider 131. Accordingly, a dimension in the axial direction of the inner slider can be reduced. As a result, the manipulation portion can be reduced to a more compact size.

In the treatment tool according to each of the embodiments of the present invention, aspects of the shaft and the clutch plate can be variously modified.

As shown in FIGS. 13A to 13C, modified examples of the clutch plate are shown. In clutch plates 171a to 171c, a diameter of a through-hole 172 is reduced in at least one end portion. Further, an edge 173 is formed at the end portion. Accordingly, when the clutch plate is inclined with respect to the shaft 44, the edge 173 comes in contact with the shaft 44. For this reason, a frictional force with the shaft is further increased to prevent slipping between the clutch plate and the shaft. As a result, the gripping force can be further securely controlled.

When the edge 173 is formed throughout a circumferential direction of the through-hole 172, as shown in FIGS. 13A and 13B, the edge 173 may be formed at any one of the end portions of the through-hole 172. As shown in FIG. 13C, the edge may be formed at both of the end portions of the through-hole 172. For example, the clutch plate 171c may be formed by joining two clutch plates having the edges 173 machined at one of the end portions of the through-holes such that the through-holes are in communication with each other.

Burrs generated when the through-hole is punched or the like may be edges. The edges need not be formed throughout the circumferential direction of the through-hole. The edges may be formed at only a region that approaches the shaft when the clutch plate is inclined.

FIGS. 14A and 14B show shafts 181a and 181b having a rectangular cross-sectional shape. Accordingly, at an apex 182, the clutch plate 71 strongly comes in contact with the shaft. For this reason, a frictional force between the clutch plate and the shaft can be increased. Since the cross-sectional shape may have an apex to obtain such an effect, the shape of the shaft is not limited to a rectangular shape. The shaft may have other polygonal cross-sectional shapes.

FIGS. 15A and 15B show a clutch plate 175 having a shape in which an inner surface of a through-hole has a plurality of convex portions 176. Even in this way, the convex portion 176 strongly comes in contact with the shaft. For this reason, the frictional force can be increased. Here, as shown in FIG. 15B, even in an inserted shaft 183, a plurality of convex portions 184 may be formed on an outer circumferential surface thereof. Examples of the component with the shape having the plurality of convex portions may include the component in which the above-described cross-sectional shape is a polygonal shape, in addition to the shaft 183. These convex portions may be combined with the clutch plate 175.

The convex portion formed in the through-hole of the shaft or the clutch plate may be formed throughout the longitudinal direction and extend without changing a phase in the circumferential direction. In this case, it is preferable that sliding of the slider in normal use is not easily prevented and an influence on a manipulation feeling can be suppressed.

Figure 16:
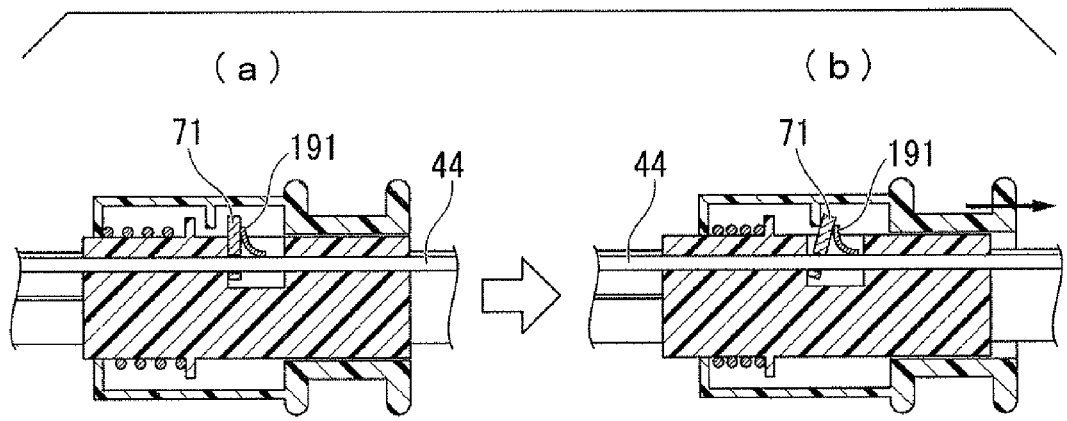
FIG. 16 is a view showing a modified example of a bias spring of the endoscope treatment tool according to each of the embodiments of the present invention.

Like a modified example shown in FIG. 16, a leaf spring 191 may be used as the bias spring. When the leaf spring is used, a dimension in the axial direction of the shaft 44 can be reduced in comparison with the case in which the above-described compression coil spring is used as the bias spring. For this reason, the slider and the manipulation portion can be easily reduced in size.

Figure 17:
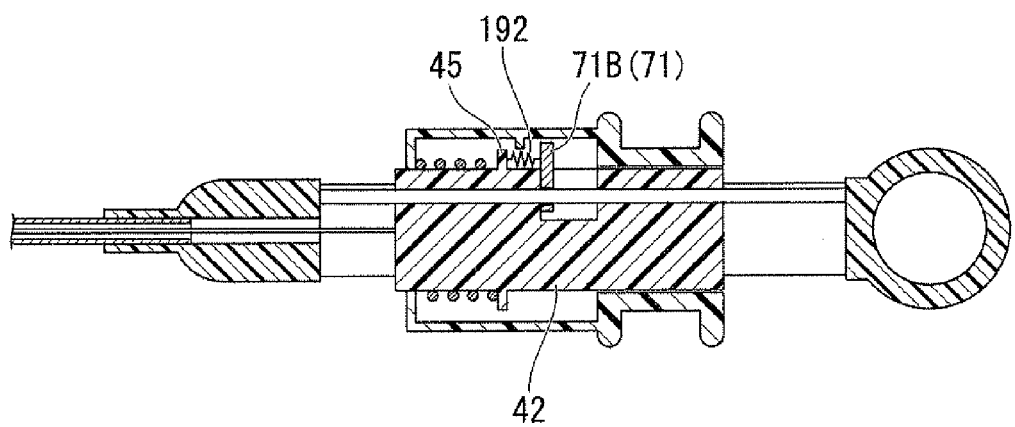
FIG. 17 is an enlarged cross-sectional view showing a modified example of the manipulation portion of the endoscope treatment tool according to each of the embodiments of the present invention.

Like a modified example shown in FIG. 17, a tension spring 192 may be used as the bias spring. The tension spring 192 connects the flange 45 of the inner slider 42 and the end portion 71B of the clutch plate 71. Accordingly, since a space in which the bias spring is disposed in the notch 46 is unnecessary, a dimension in the axial direction of the inner slider 42 can be reduced. As a result, the manipulation portion can be easily reduced in size.

Figure 18:
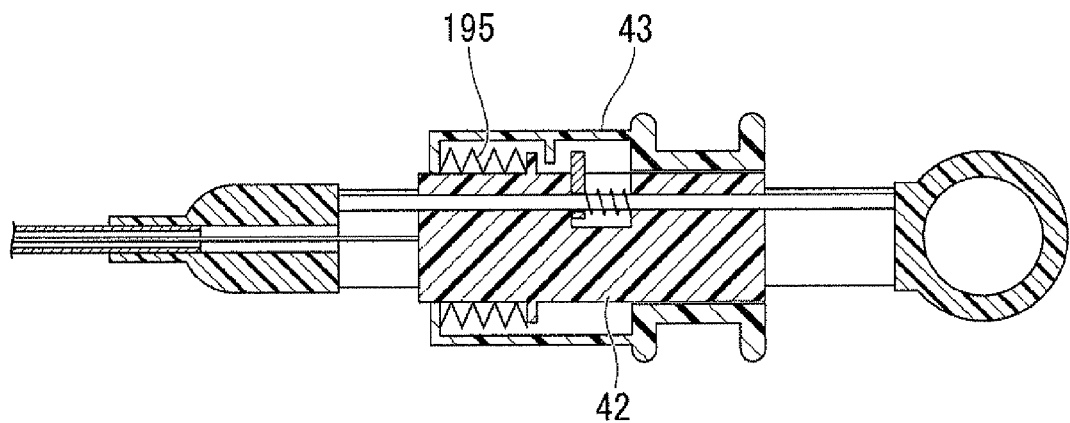
FIG. 18 is an enlarged cross-sectional view showing a modified example of the manipulation portion of the endoscope treatment tool according to each of the embodiments of the present invention.
Figure 19:
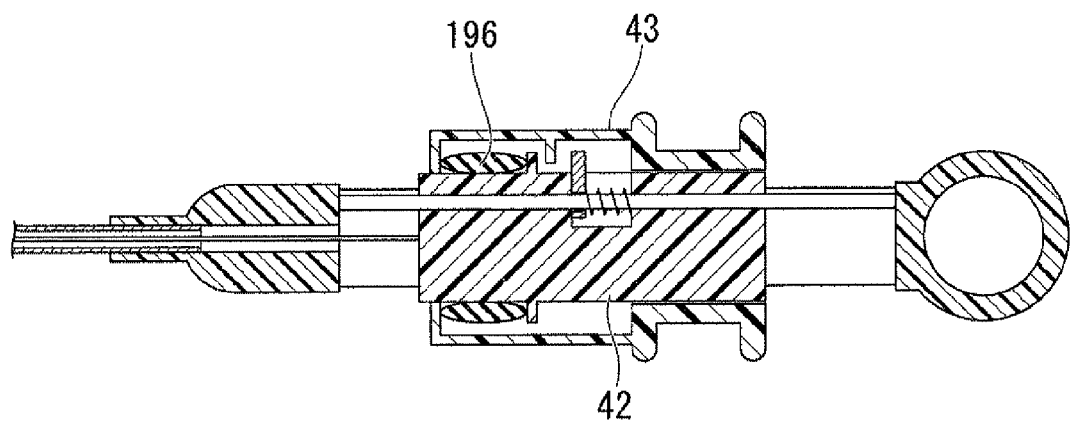
FIG. 19 is an enlarged cross-sectional view showing a modified example of the manipulation portion of the endoscope treatment tool according to each of the embodiments of the present invention.

The force adjustment member configured to hold a positional relation between the outer slider and the inner slider is not limited to the above-described coil spring. A leaf spring 195 shown in FIG. 18 or an elastic body 196 shown in FIG. 19 may be used as the force adjustment member. Since these members generally have a larger spring constant than that of a coil spring, a large spring force can be obtained with a small amount of movement. For this reason, a dimension in the axial direction of the inner slider and the outer slider can be reduced. As a result, the manipulation portion can be easily reduced in size.

A structure of the treatment tool according to each of the embodiments of the present invention may be applied to a treatment tool configured to apply an electric current to a treatment portion upon use. In this case, a known plug or the like configured to connect with the power source may be provided to apply an electric current to the treatment portion through, for example, the manipulation wire or the like.

While preferred embodiments of the present invention have been described, the present invention is not limited to the embodiments. Additions, omissions, substitutions, and other modifications can be made to the present invention without departing from the spirit and scope of the present invention. The present invention is not limited to the above-described description, and is only limited by the scope of the appended claims.

What is claimed is:

1. An endoscope treatment tool comprising:
   a treatment portion which is provided at a distal end of the endoscope treatment tool;
   a manipulation portion which is configured to manipulate the treatment portion; and
   a manipulation wire which connects the treatment portion and the manipulation portion, wherein
   the manipulation portion includes:
      a manipulation portion main body;
      a shaft which is attached to the manipulation portion main body and extends parallel to the manipulation portion main body;
      a clutch plate which has a through-hole into which the shaft is slidably inserted;
      a manipulation member which is slidably attached to the manipulation portion main body so as to manipulate the manipulation wire; and
      a force adjustment member which is compressed in accordance with manipulation of the manipulation member, and
   the clutch plate is inclined with respect to the shaft such that a first axis of the through-hole is non-parallel to a second axis of the shaft in accordance with compression of the force adjustment member, and thereby the manipulation member is fixed to the manipulation portion main body by the clutch plate which is fixed to the shaft so as not to slide with respect to the shaft.

2. The endoscope treatment tool according to claim 1, wherein
the manipulation portion further includes a posture holding member which is configured to hold a posture of the clutch plate such that the first axis of the through-hole is parallel to the second axis of the shaft, and
a posture holding by the posture holding member is released in accordance with the compression of the force adjustment member, and thereby the clutch plate is inclined with respect to the shaft.

3. The endoscope treatment tool according to claim 2, wherein
the manipulation member includes:
a first slider which is connected to the manipulation wire and is slidably attached to the manipulation portion main body and the shaft; and
a second slider which is slidably attached to the first slider, and
the second slider is retracted with respect to the first slider, and thereby the force adjustment member is compressed.

4. The endoscope treatment tool according to claim 3, wherein
the treatment portion is a pair of forceps members which is supported by a rotation shaft such that the forceps members freely rotate relative to each other.

5. The endoscope treatment tool according to claim 4, wherein
an end portion of the clutch plate comes in contact with the second slider, and thereby the clutch plate is inclined with respect to the shaft.

6. The endoscope treatment tool according to claim 4, wherein
the end portion of the clutch plate projects over an outer circumferential surface of the first slider.

7. The endoscope treatment tool according to claim 4, wherein
the shaft and the manipulation wire are concentrically disposed.

8. The endoscope treatment tool according to claim 4, wherein
the posture holding member is a bias spring biasing the clutch plate in a predetermined direction.

* * * * *